United States Patent [19]
Roychowdhury

[11] Patent Number: 5,681,522
[45] Date of Patent: Oct. 28, 1997

[54] METHOD AND APPARATUS FOR ANNEALING ANGIOPLASTY BALLOONS TO IMPROVE RE-WRAPPABILITY THEREOF

[75] Inventor: Suranjan Roychowdhury, Minnetonka, Minn.

[73] Assignee: Schneider (USA) Inc., Minneapolis, Minn.

[21] Appl. No.: 625,945

[22] Filed: Apr. 1, 1996

[51] Int. Cl.$^6$ .................. B29C 49/08; B29C 49/64
[52] U.S. Cl. .................. 264/532; 264/573; 264/230; 264/235; 264/342 R; 264/346; 264/900; 604/96; 606/194
[58] Field of Search .................. 264/516, 523, 264/532, 573, 900, 904, 230, 235, 342 R, 345, 346; 604/96; 606/194

[56] References Cited

U.S. PATENT DOCUMENTS

| | | | |
|---|---|---|---|
| 5,015,231 | 5/1991 | Keith et al. | 604/96 |
| 5,053,007 | 10/1991 | Euteneuer | 604/96 |
| 5,137,512 | 8/1992 | Burns et al. | 604/96 |
| 5,425,710 | 6/1995 | Khair et al. | 606/194 |

*Primary Examiner*—Catherine Timm
*Attorney, Agent, or Firm*—Haugen and Nikolai, P.A.

[57] ABSTRACT

To improve the re-wrappability of the expander members used on balloon catheters subsequent to an initial inflation thereof, the balloon member is subjected to an annealing process in which the balloon member, in its wrapped configuration, is placed within a plastic sheath and it, together with the sheath, is then placed between the jaws of a clamping fixture where the jaws may be heated to a predetermined temperature. When the jaws are made to close on the sheath and the wrapped balloon contained within it, the wrapped balloon is subjected to a radial compressive pressure and a temperature approximately equal to or above the glass transition temperature for the balloon material utilized and then maintained at that temperature for a predetermined time interval. The annealing is found to introduce a memory component into the plastic of the balloon that causes it to assume a lower profile upon deflation than otherwise obtained.

16 Claims, 3 Drawing Sheets

METHOD AND APPARATUS FOR ANNEALING ANGIOPLASTY BALLOONS TO IMPROVE RE-WRAPPABILITY THEREOF

BACKGROUND OF THE INVENTION

I. Field of the Invention

This invention relates generally to the manufacture of expander members for balloon catheters, and more particularly to a method and apparatus for annealing a pre-made expander member so as to enhance the ability of a previously inflated expander member to be collapsed about a catheter body member on which it is mounted to facilitate its withdrawal into the distal end of a guide catheter or subsequent manipulation in the vasculature in an angioplasty procedure.

II. Discussion of the Prior Art

The use of balloon catheters for coronary angioplasty is known in the art. In an angioplasty procedure, an occluded blood vessel, i.e., one containing a stenosis, is treated by the inflation of a balloon member which expands the vessel lumen thus pressing the stenotic lesion back against the vessel wall. Typically, the expander member or balloon is carried on the distal end of a dilatation catheter which is routed through a guide catheter that had been previously advanced through the vascular system to a location that is proximal to, for example, a coronary artery containing a stenotic lesion. Following placement of the expander member across the lesion as desired, fluid is introduced into the proximal end of the catheter to inflate the expander member to a relatively high pressure, thereby restoring patency to the vessel.

Coronary angioplasty procedures and angioplasty devices are described in detail in Vliestra et al., "Coronary Balloon Angioplasty," Blackwell Scientific Publications (1994).

Medical balloons that are known in the art are disclosed in the following documents: U.S. Pat. No. Re 32,983 to Levy and U.S. Pat. Nos. 4,906,244, 5,108,415, 5,156,612, 5,236,659 and 5,304,197 to Pinchuk. (All documents cited herein, including the foregoing, are incorporated herein in their entireties for all purposes.)

Angioplasty balloons have been fabricated from a variety of thermoplastic materials, one being polyethylene terephthalate (PET). PET balloons are generally manufactured by inserting a parison in a heated mold and by radially and longitudinally stretching the parison while it is in a rubbery state to achieve a balloon that is biaxially oriented and which exhibits relatively low compliance at elevated pressures and a high burst strength. Following fabrication of the expander member, it is mounted near the distal end of a catheter body member so as to span or overlay an inflation port that extends through the wall of the catheter body and into an inflation lumen that extends to the proximal end of the catheter.

Prior to its inflation while treating a stenotic lesion, the balloon or expander member is tightly wrapped or folded so as to exhibit a low profile at the distal end of the angioplasty catheter. This facilitates its ability to be routed through the lumen of a guide catheter and into a coronary artery for placement adjacent the lesion to be treated. Once the balloon has been inflated by injecting an inflation fluid through the inflation lumen and out the inflation port, balloons fabricated from PET generally exhibit a tendency towards "winging" or "pancaking" upon evacuation of the inflation fluid. That is to say, evacuation of the inflation fluid does not result in the balloon member again tightly re-wrapping and conforming to the periphery of the catheter body. This makes it difficult to withdraw the distal end portion of the catheter back into the lumen of the guide catheter with which it is used or to perform additional manipulation of the balloon catheter within the vasculature.

A need, therefore, exists for a method or process for treating angioplasty balloons to impart a memory property to the plastic so that upon deflation following inflation, the balloon will collapse about the catheter body to assume a low profile, e.g., reduced winging or pancaking.

SUMMARY OF THE INVENTION

The present invention is concerned with a method for annealing inflatable expander members used on intravascular catheters for reducing their rewrapped profile upon deflation thereof following initial inflation. In carrying out the method, an expander member may be formed using known technology from a thermoplastic polymer in a stretch/blow-molding operation. The thus fabricated expander member mounted either on a catheter body or on a temporary mandrel is subsequently placed within an outer, flexible sheath and the sheath containing the expander member is subjected to an elevated temperature and pressure. For example, the sheath containing the wrapped balloon may be inserted between cooperating jaws of a clamping/heating fixture. The jaws are heated to a predetermined temperature well below the melting point of the plastic involved and preferably at or slightly above the glass transition temperature. For PET, the glass transition is in the range of from about 70° C. to about 80° C. With the jaws closed to apply a predetermined pressure to the sheath and its contents that temperature is maintained for a predetermined period of time. Following this annealing step, the clamping jaws are opened and the sheath containing the expander member is removed, such that the annealed expander member can later be attached to the catheter body member, if it is not already so attached.

The pressure and elevated temperature may also be applied to an angioplasty balloon by inserting same in a compliant sheath contained within a pressure vessel that also holds a heated fluid. By increasing the fluid pressure within the vessel, radial inwardly directed forces are directed through the sheath to the wrapped balloon.

DESCRIPTION OF THE DRAWING

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
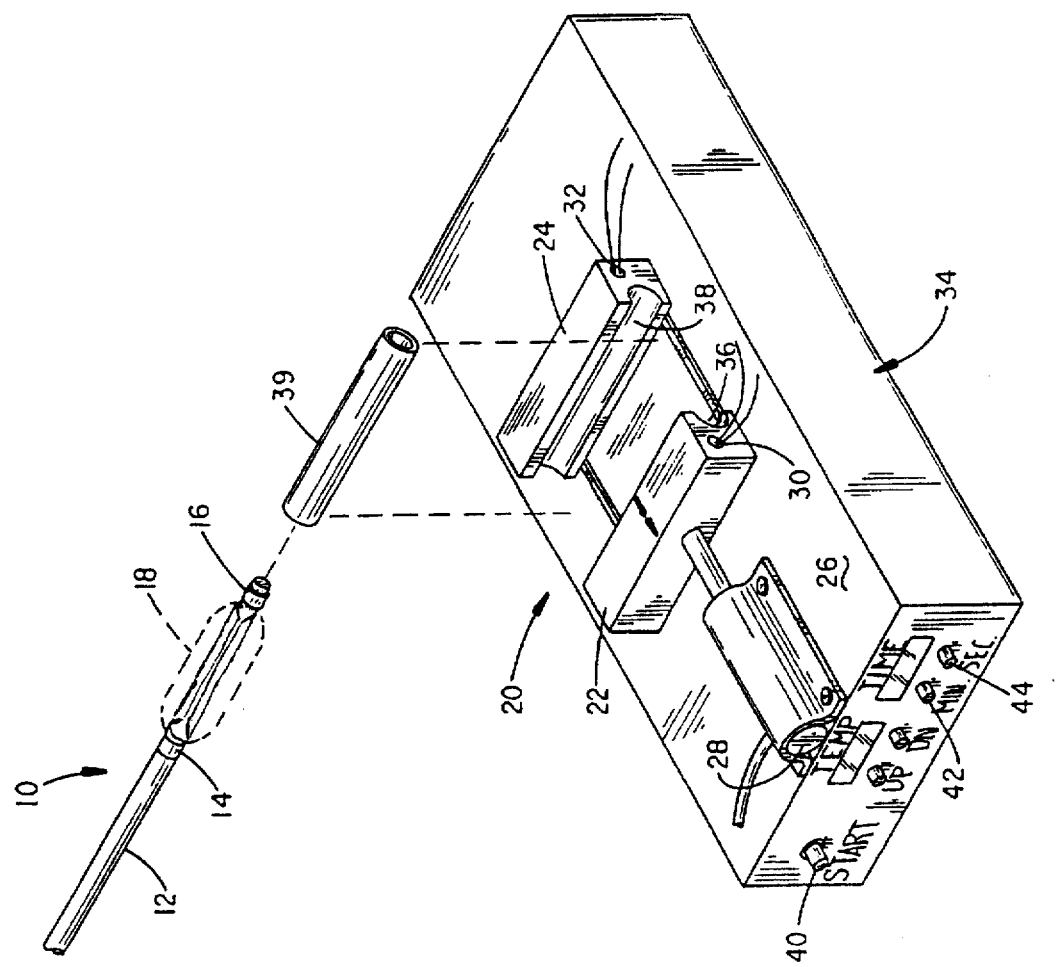
FIG. 1 is a perspective view of one apparatus used in carrying out the method of the present invention.

FIG. 1 shows one type of apparatus used for annealing angioplasty balloons to impart a desired memory property into the plastic comprising the balloon in a way that enhances the re-wrappability of the balloon about the catheter body on which it is mounted following its inflation and subsequent deflation. By annealing the balloon, it can be made to more closely conform to the outer periphery of the catheter body about which it is wrapped, thus facilitating subsequent manipulation, for example, its retraction into a guide catheter upon its removal from the patient at the conclusion of an angioplasty or other diagnostic procedure in which the balloon catheter is employed.

In FIG. 1, a distal end portion of a balloon catheter is indicated generally by numeral 10 and is seen to include a tubular plastic body member 12 which has an expander member or balloon bonded to it at 14 and 16. The balloon is located so as to span an inflation port (not shown) leading to a lumen that extends back to the proximal end of the catheter and to a fitting on the hub of the catheter to which a source of fluid under pressure may be connected. In this fashion, the expander member can be made to inflate from the wrapped condition shown in solid line in FIG. 1 to an inflated condition represented by the dashed lines 18.

During the course of an angioplasty procedure, it becomes necessary to deflate the balloon by evacuating the previously injected inflation fluid from the balloon and, ideally, the balloon will rewrap itself about the catheter body 12 and thereby present a low profile, permitting it to be drawn back into a guide catheter, or otherwise manipulated in the vasculature. However, with balloons made from PET, and to some extent with balloons fabricated from other polymers, there is a tendency for the balloon to assume a flat arrowhead shape that makes it difficult to fit into the lumen of the guide catheter, or to negotiate tortuosity or tapered segments in the vasculature or previously implanted vascular prostheses, e.g., stents. This makes subsequent manipulation difficult.

In accordance with the present invention, the angioplasty balloon is annealed to impart to it a memory property that enhances the re-wrappability of the deflated balloon about the catheter body on which it is mounted. In carrying out the method, the apparatus illustrated in FIG. 1 may be employed. It comprises a clamping assembly indicated generally by numeral 20 having a pair of solenoid actuated jaws 22 and 24 slidably mounted on a base plate 26. The jaw 24 may be stationary while jaw 22 is reciprocally movable toward and away from the stationary jaw 24. An air or electrical solenoid 28 is operatively connected to the movable jaw 22 to impart the translational movement thereof. However, those skilled in the art will recognize that there are many different ways available for moving the clamping jaws. Incorporated into the clamping jaws 22 and 24 are cal rods 30 and 32 which are adapted to be connected to a source of electrical energy (not shown) contained within the housing 34 to allow controlled heating of the jaws. Suitable temperature sensors, such as thermistors (not shown), are operatively coupled to the jaws 22 and 24 and connect to the control circuitry to provide a feedback signal that can be compared to a set-point so that the current delivered to the cal rods 30 and 32 can be controlled to equal the desired set-point temperature.

The jaws 22 and 24 each contain a semicircular recess, as at 36 and 38, of a predetermined diameter substantially corresponding to the diameter of the catheter body 12 when overlaid with the wrapped film comprising the expander member.

Before the collapsed balloon is placed between the jaws 22 and 24 of the clamping/heating fixture 20, it is placed in a sheath 39 which may preferably comprise an elastomeric material whose melting point is substantially above the desired annealing temperature set into the fixture 20.

Alternatively, the sheath 39 may comprise a non-elastomeric material. Once the sheath 39 has been wrapped about the catheter's expander member, the two are positioned between the jaws of the fixture and a start button 40 is actuated. Actuation of the start button 40 will cause the solenoid 28 to advance the movable jaw 22 toward the fixed jaw 24 thereby clamping the sheath 39 and the prewrapped expander member within the confines of the semicircular recesses 36 and 38. The expander member will have heat energy conducted to it through the sheath 39 for a period of time previously set into the fixture 20 by the push buttons 42 and 44. When the preset time interval has elapsed, the solenoid 28 is again actuated, opening the jaw 22 relative to the fixed jaw 24. At this point, the catheter 10 is removed from the sheath 39 prior to packaging and sterilization.

Assuming that the expander member of the catheter is fabricated from PET, the temperature to which the sheath and expander member are subjected generally lies between about the glass transition temperature of PET (between about 70° C. and 80° C.) to about 130° C. The time interval over which the annealing takes place may range between as low as about one-half minute and as high as about two hours. The apparatus 20 is arranged to subject the sheath and its contents to pressures ranging from about 5–500 psi.

An alternative expander member material may be any suitable thermoplastic polymer including, but not limited to, nylon and polyethylene.

While the sheath 39 may comprise any suitable plastic, it has been found expedient to employ a heat shrinkable compliant plastic which, upon exposure to an elevated temperature, will constrict and thereby subject the wrapped expander member to rather uniform, inwardly-directed, radial forces and substantially conform to the shape of the wrapped expander member. Non-elastomeric sheath materials can include, but need not be limited to, fluoropolymers, such as PTFE, FEP and TFE. Elastomerics can include silicone rubbers and fluorosilicones. Preferably, the sheath will not adhere to the expander member as a result of the annealing process.

It is contemplated that the expander member can be preaffixed to a catheter body stock 12 before the annealing process of the present invention is carried out. Alternatively, a preformed expander member may be temporarily mounted on a removable mandrel before being placed in the sheath 39 and between the heated jaws 22 and 24 of the annealing apparatus.

Figure 2:
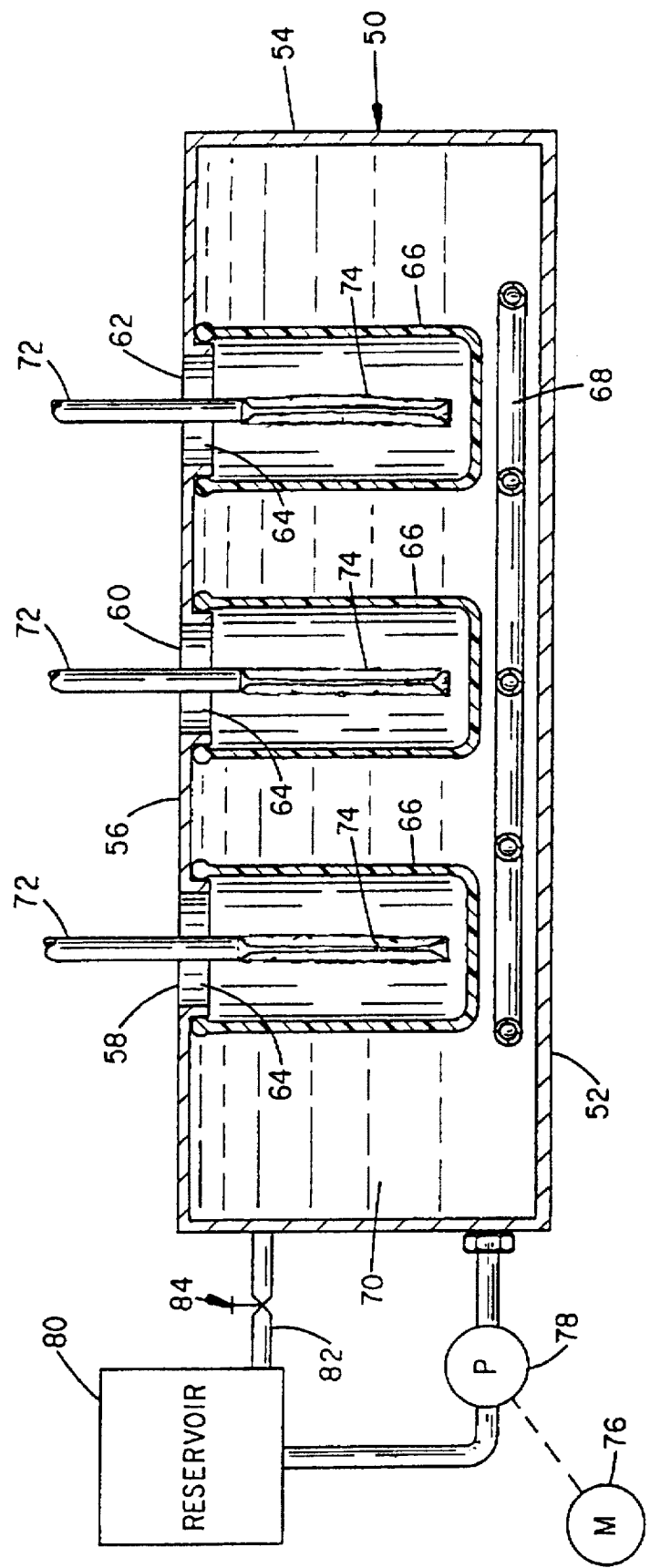
FIG. 2 is a schematic diagram of an alternative apparatus useable in carrying out the method of the present invention.

FIG. 2 is a schematic representation of an alternative apparatus for carrying out the balloon annealing method of the present invention. There is identified by numeral 50 a temperature controlled pressure vessel having a bottom wall 52, a side wall 54 and a top wall 56. Top wall 56 has a plurality of openings formed therein, as at 58, 60 and 62, and surrounding each opening is a downwardly depending circular flange or collar as at 64. Fitted onto to the collars 64 surrounding each of the openings is the open end of an otherwise closed, elongated, compliant, silicon rubber sleeve 66. The vessel 50 includes a serpentine wound electrical heater element 68 and the volume of the vessel is filled with an incompressible fluid, such as an oil 70. Alternative fluids include, but are not limited to, substantially incompressible fluids, such as water or ethylene glycol. In certain embodiments, compressible fluids, such as an inert gas (e.g., argon) can be used. The heater 68 and conventional PID control circuitry (not shown) are arranged to maintain the oil 70 at a desired predetermined temperature. It can be seen in FIG. 2 that there is inserted through the openings 58, 60 and 62 in the sleeves 66, a cylindrical substrate, as at 72. This substrate may either comprise a catheter body to which is affixed an expander member in forming a balloon catheter or, alternatively, a pre-made expander member may be mounted on a temporary cylindrical mandrel and inserted into the tubular sleeves 66.

In carrying out the annealing process to enhance re-wrappability of the balloons about the catheter on which they are ultimately affixed, a means is provided for pressurizing the vessel 50 so as to deform and collapse the tubular sleeves 66 about the wrapped expander members 74 so as to expose the expander members to a predetermined pressure and temperature for a predetermined time interval. In FIG. 2 the pressurization means is shown as including a motor 76 driving a pump 78 whose inlet is connected to a reservoir 80 that contains the same type of oil as is in the vessel 50. A conduit 82 having a pressure relief valve 84 in it joins the reservoir 80 to the interior of the pressure vessel 50. When it is desired to pressurize the vessel 50, the pressure relief valve 84 is closed and the motor 76 is energized to pump additional fluid from the reservoir 80 into the pressure vessel 50 so as to collapse and compress the sleeves 66 about the wrapped expander members 74 that are positioned within the sleeves. With the silicone rubber sleeves in intimate contact with the expander members, heat is transferred through the wall of the sleeves to the wrapped expander members while the controlled pressure is applied.

At the conclusion of the annealing operation, the motor 76 will be turned off and the pressure relief valve 84 opened so as to allow the pressurized fluid 70 within the vessel 50 to return to the reservoir, thereby relieving the compressive forces applied via the sleeves 66 to the wrapped expander members 74.

It is also contemplated that instead of employing a motor and pump combination, the pressure vessel 50 could be equipped with a displaceable piston in one of the walls 52 or 54. By actuating the piston, the volume of the pressure vessel 50 would effectively be reduced, thereby compressing the flexible silicon rubber sleeves 66 about the wrapped expander members contained within the sleeves.

EXAMPLE

Previously formed PET expander members nominally measuring 4.0×40 mm when expanded were used in a study. A total of 15 catheter expander members were obtained and divided into three groups of five each. Two groups were subjected to separate annealing conditions, while the third group was left untreated as a control. After the annealing treatment, evaluation was carried out as follows:

Each balloon was passed through a short segment of a 7 Fr. guide catheter, consisting of the distal section of the guide. The inflation member was subsequently inflated to rated burst pressure (10 atm./147 psi) and held at this pressure for 30 seconds. Subsequently, the balloon was deflated and pulled back through the guide segment. The balloon profile was then recorded using a laser micrometer. Four measurements were taken on each balloon by rotating the expander members incrementally by 90° and using a laser micrometer.

Figure 3:
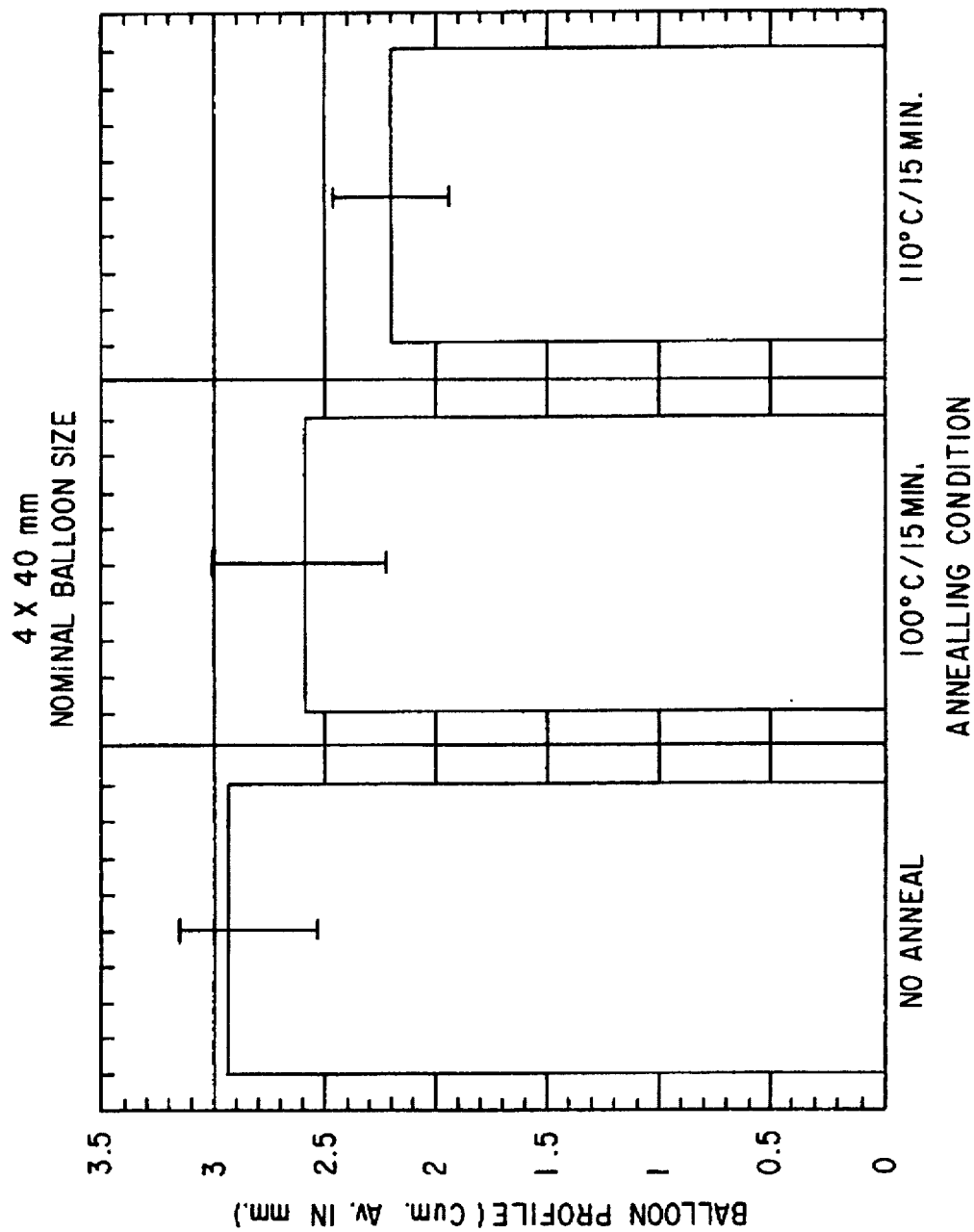
FIG. 3 is a bar graph showing the effects of annealing on the balloon profile following expansion and subsequent re-wrapping.

FIG. 3 is a bar graph showing the difference in the average re-wrapped balloon profile with no annealing, with annealing at 100° C. for a time interval of 15 minutes and for annealing at 110° C. for 15 minutes. The graph clearly indicates that subjecting the wrapped balloons to elevated temperatures and pressures for predetermined time intervals significantly reduces the re-wrapped profile thereof compared to the result when no annealing is employed.

It was concluded from the results of this study and from visual observations that the annealing treatment confers a memory effect to PET balloons. This effect causes the balloon to try to return to its original, wrapped shaped when an external stimulus (vacuum and being pulled back into a guide catheter) is applied, resulting in a reduced overall balloon profile. The untreated PET balloons continued to manifest a flat, "arrowhead" (zero rewrap) configuration under similar conditions.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for preparing inflatable expander members used on intravascular catheters for reducing their rewrapped profile upon deflation thereof following initial inflation, comprising the steps of:

(a) forming an expander member comprising PET;

(b) placing the expander member formed in step (a) within an outer compliant sheath;

(c) inserting the sheath containing the expander member in a pressure applying means;

(d) actuating the pressure applying means to apply radially directed forces to the sheath and expander member;

(e) heating the pressure applying means to a predetermined temperature at least equal to the glass transition temperature of PET;

(f) maintaining the pressure applying means at said predetermined temperature for a predetermined time interval in a range of from about one-half minute to two hours;

(g) removing the sheath containing the expander member from the pressure applying means; and (h) extracting the expander member from the sheath.

2. The method as in claim 1 wherein step (e) is performed prior to step (c).

3. The method as in claim 1 wherein the sheath is a heat-shrinkable thermoplastic.

4. The method as in claim 1 wherein the sheath is a non-elastomeric fluoropolymer material.

5. The method as in claim 1 and further including the step of affixing the expander member to a tubular catheter body following step (a) and prior to step (b).

6. The method as in claim 1 and further including the step of mounting the expander member on a tubular substrate following step (a) and prior to step (b) and subsequently removing the expander member from the tubular substrate and affixing the expander member to a tubular catheter body following step (h).

7. A method for preparing inflatable expander members used on intravascular balloon catheters for reducing their rewrapped profile upon deflation thereof following initial inflation, comprising the steps of:

(a) forming an expander member from polyethylene terephthalate in a stretch blow molding operation;

(b) wrapping the expander member on a tubular substrate to minimize the radial profile of the expander member;

(c) placing the expander member within a compliant plastic sheath;

(d) inserting the sheath containing the expander member between cooperating jaws of a clamping fixture;

(e) applying pressure to the sheath and expander;

(f) heating the jaws of the clamping fixture to a temperature of at least 70° C. and not more than 130° C. and maintaining that temperature for a predetermined time interval;

(g) removing the sheath containing the expander member from between the jaws of the clamping fixture; and (h) extracting the expander member from the sheath.

8. The method as in claim 7 wherein step (f) is performed prior to step (e).

9. The method as in claim 7 wherein the tubular substrate comprises a tubular catheter body.

10. The method as in claim 7 wherein the tubular substrate is a temporary mandrel.

11. The method as in claim 7 wherein the pressure applied to the sheath and expander member is compressive and in the range from about 5 psi to 500 psi.

12. A method for annealing inflatable expander members used on intravascular catheters for reducing their rewrapped profile upon deflation thereof following initial inflation, comprising the steps of:

(a) forming an expander member comprising PET;

(b) applying radial compressive pressure in a range of from 5 psi to 500 psi to the expander member; and (c) maintaining the radial compressive pressure at a predetermined temperature at least equal to the glass transition temperature of PET for a predetermined time interval in a range of from 30 seconds to 120 minutes.

13. The method as in claim 12 including the further step of wrapping the expander member on a tubular substrate prior to step (b).

14. The method of claim 13 and further including the step of inserting the substrate with the expander member wrapped therein in a compliant outer sheath prior to step (b).

15. The method of claim 12 wherein the predetermined temperature is in a range of from about 70° C. to 130° C.

16. The method of claim 15 wherein the predetermined temperature is in a range of from about 70° C. to 110° C.

* * * * *

UNITED STATES PATENT AND TRADEMARK OFFICE
CERTIFICATE OF CORRECTION

PATENT NO. : 5,681,522
DATED : October 28, 1997
INVENTOR(S) : Suranjan Roychowdhury It is certified that error appears in the above-indentified patent and that said Letters Patent is hereby corrected as shown below:

Column 7, line 3, after "expander" insert -- member --.

Signed and Sealed this

Twenty-seventh Day of January, 1998

BRUCE LEHMAN

*Attest:*

*Attesting Officer*       *Commissioner of Patents and Trademarks*